(12) United States Patent
Watanabe et al.

(10) Patent No.: US 6,814,917 B1
(45) Date of Patent: Nov. 9, 2004

(54) ALUMINA SINTERED BODY AND PROCESS FOR PRODUCING THE SAME

(75) Inventors: Hisashi Watanabe, Tsukuba (JP); Yoshio Uchida, Tsukuba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/361,118

(22) Filed: Jul. 27, 1999

(30) Foreign Application Priority Data

Jul. 29, 1998 (JP) .......................................... 10-213947
Dec. 15, 1998 (JP) .......................................... 10-356002

(51) Int. Cl.$^7$ ................................................ H05B 6/00
(52) U.S. Cl. ...................................... 264/434; 264/681
(58) Field of Search ................................ 264/434, 681

(56) References Cited

U.S. PATENT DOCUMENTS

| | | | |
|---|---|---|---|
| 4,799,601 A | 1/1989 | Shimai et al. ............ 220/21 R |
| 4,919,868 A | * 4/1990 | Huang | |
| 5,411,583 A | 5/1995 | Bennison et al. ........ 106/14.05 |
| 5,672,554 A | 9/1997 | Mohri et al. ................ 501/127 |
| 5,688,450 A | * 11/1997 | Ali et al. | |
| 6,258,440 B1 | * 7/2001 | Aihara et al. ............... 428/141 |

FOREIGN PATENT DOCUMENTS

| | | |
|---|---|---|
| EP | 0 678 489 | 10/1995 |
| EP | 0 708 065 | 4/1996 |
| JP | 5-279114 | 10/1993 |
| JP | 8-290962 | 11/1996 |
| JP | 9-2864 | 1/1997 |
| JP | 10-67554 | 3/1998 |

OTHER PUBLICATIONS

Dictionary of Ceramic Science and Engineering by O'Bannon, Plenum Press 1984, p. 262.*
Patent Abstracts of Japan vol. 14, No. 562 (C–0788), Dec. 13, 1990 and JP 02 243561 A (NGK Spark Plug Co. Ltd., Sep. 27, 1990.
Chemical Abstracts, vol. 126, No. 5, Feb. 3, 1997 Columbus, OH, US; abstract No. 63911; Mohri, Masahide et al; "Development of advanced alumina—Sumicorundum." XP002120496 & Sumito Kagaku (Osaka ) (1996), (2), Apr. 14, 1996.

* cited by examiner

*Primary Examiner*—Peter Chin
(74) *Attorney, Agent, or Firm*—Sughrue Mion, PLLC

(57) ABSTRACT

A process for producing a polycrystalline alumina sintered body which includes the steps of: subjecting alumina powder to ultrasonic irradiation, mechanical stirring not using a grinding medium, or ultrasonic irradiation and mechanical stirring not using a grinding medium, resulting in slurry dispersed in a solvent; drying and forming the slurry to produce a green body; and then sintering the green body in an air atmosphere at a temperature in the range of 1400° C. to 1800° C.; wherein the alumina powder has: a purity of 99.99 wt % or more and includes α alumina particles having polyhedral shape, having substantially no red surface and a D/H ratio of from 0.5 or more to 3.0 or less; the number-average particle size of from 0.1 $\mu$m or more to 1.0 $\mu$m or less; and a D90/D10 ratio of 7 or less.

8 Claims, No Drawings

ALUMINA SINTERED BODY AND PROCESS FOR PRODUCING THE SAME

BACKGROUND OF THE INVENTION

1. Field of the Invention

The present invention relates to an alumina sintered body and a process for producing the same. Said alumina sintered body is suitable for members required to have a corrosion resistance which are mainly in contact with a corrosive solution and gas, or products easily affected by adhesion or adsorption of dust particles of instruments for semiconductor manufacturing, such as vacuum chuck, pincette, and hands used for operations including cleaning, transferring, and surface processing of a silicon wafer; or products required to be pore-free, such as materials for a substrate for a hard disk, a substrate for a magnetic head, and the like, materials for various kinds of industrial mirrors, and the like, and bioceramics materials for artificial tooth, artificial femoral head, and the like.

2. Prior Art

For the constituents in a semiconductor manufacturing process, ceramics materials are generally used for avoiding mixing of metallic elements into a silicon wafer, and contamination. The sintered bodies of alumina and silicon carbide are commonly used as the ceramic materials. The sintered bodies of alumina and zirconia are also used for bioceramics such as artificial tooth, artificial femoral head and artifical nee in view of mixing of metals into a living body, wear resistance, and the like.

The conventional raw material powder such as alumina or silicon carbide in the foregoing applications has a problem that the powder comprises fine particles whose primary particles are 0.5 $\mu$m or less and it is non-uniform powder having a spheroidal form or having fractured surfaces. Further, the inside of each particle is also non-homogeneous and have a large number of defects. The powder has a wide particle size distribution and contains a large number of coarse aggregated particles. These cause the formation of pores in a sintering process. As a method for reducing the pores, there have been commonly a method in which several sintering agents are added. However, a sintered body with sufficiently high fired density and less pores cannot be obtained.

The ceramics sintered body product for components of a semiconductor manufacturing system is used by mirror-polishing its portion to be in contact with a silicon wafer. The ceramics sintered body product manufactured from the conventional raw material powder has problems that the wafer is marred by foreign substances such as dust particles adhered to the pore of the sintered body, or the edge of the pore, and the like.

Further, when the silicon wafer or the like supported on the ceramics sintered body having a large number of pores is subjected to processing such as heat treatment or plasma etching, this arises a problem that there occurs falling off of particles, or elution of impurities such as Na from the ceramics in the vicinity of the pores to contaminate the wafer.

The foregoing problems have further become important with the progress of achieving higher density and higher integration of a semiconductor device. Accordingly, a sintered body with high purity and high density, and less pores has been required.

Also, in bioceramics such as artificial tooth, artificial femoral head and artifical nee, the ceramic materials or polymer materials used in a pair therewith are worn out by the edge of the pore in the polished surface. This results in the formation of fine particles to cause pain to a human body. Further, these pores become the starting points of fracture to lower the strength of the sintered body and reliability of the product.

To overcome these problems, there are disclosed plasma-resistant fluorine alumina ceramics and the manufacturing method thereof in Japanese Laid-Open Patent Publication No. 9-2864. In Japanese Laid-Open Patent Publication No. 9-2864, silicon oxide and calcium oxide are added therein in a large amount of 0.3 to 0.7 wt % for reducing the area % of the unsintered particle. Thus, there still has a problem about the corrosion resistance in hot water, an acid solution or an alkaline solution. Further, it is generally known that a sintered body having a small number of pore can be obtained by hot isostatic press. However, there still has a problem industrially that it is required to sinter at high temperatures and high pressures.

SUMMARY OF THE INVENTION

The present inventors have found that a high purity alumina sintered body with extremely less pores can be obtained by using the specific alumina powder as a raw material and calcining said alumina in an air atmosphere, and the productivity thereof is high, and have completed the present invention.

That is, the present invention relates to (1) a process for producing a polycrystalline alumina sintered body which comprises the steps of:

subjecting alumina powder to ultrasonic irradiation, mechanical stirring not using a grinding medium, or ultrasonic irradiation and mechanical stirring not using a grinding medium, resulting in slurry dispersed in a solvent;

drying and forming said slurry to produce a molded body; and then sintering said green body in an air atmosphere at a temperature in the range of 1400° C. to 1800° C.;

wherein said alumina powder having a purity of 99.99 wt % or more comprises a polyhedral particle having substantially no fractured surface, and comprises a alumina particles having polyhedral shape; a D/H ratio of from 0.5 or more to 3.0 or less, wherein D represents a maximum particle diameter parallel to the hexagonal lattice plane of a hexagonal close packed lattice of a alumina, and H represents a maximum particle diameter perpendicular to the hexagonal lattice plane of a hexagonal close packed lattice of a alumina; the number-average particle size of from 0.1 $\mu$m or more to 1.0 $\mu$M or less; a D90/D10 ratio of 7 or less, wherein D10 and D90 are the particle sizes at 10% cumulation diameter and 90% cumulation diameter, respectively, from the smallest particle side in a cumulative particle size distribution.

Also, the present invention relates to a process described in (1), wherein an alumina powder added a sintering assistant is subjected to ultrasonic irradiation, mechanical stirring not using a grinding medium, or ultrasonic irradiation and mechanical stirring not using a grinding medium, resulting in a slurry dispersed in a solvent.

DETAILED DESCRIPTION OF THE INVENTION

Below, the present invention will now be described in detail.

In the present invention, alumina powder used as a raw material is alumina having a purity of 99.99 wt % or more, having substantially no fractured surface, and the residue on the sieve is in an amount of 100 ppm or less when wet sieving is performed by using a 5-μm-mesh filter. The alumina powder comprises a alumina particles having a polyhedral shape; a D/H ratio of from 0.5 or more to 3.0 or less, preferably of from 0.8 or more to 1.5 or less, wherein D represents a maximum particle diameter parallel to the hexagonal lattice plane of a hexagonal close packed lattice of α-alumina, and H represents a maximum particle diameter perpendicular to the hexagonal lattice plane of a hexagonal close packed lattice of α-alumina. The number-average particle size of the α alumina particles is from 0.1 μm or more to 1.0 μm or less, preferably of from 0.2 μm or more to 0.7 μm or less. Further, the α alumina particles have a D90/D10 ratio of 7 or less, which is a particle size distribution, wherein D10 and D90 are the particle sizes at 10% cumulation diameter and 90% cumulation diameter, respectively, from the smallest particle side in a cumulative particle size distribution.

Examples of the above-described alumina powder include α alumina powder obtained by calcining transition alumina, or alumina powder which can be changed to transition alumina by heat treatment, in an atmospheric gas containing hydrogen chloride. The α alumina powder can be obtained by, for example, a method described in Japanese Laid-Open Patent Publication No. Heisei 6-191836.

When the average particle size of the primary particles of the alumina powder used as raw material exceeds 1.0 μm, the degree of sintering is reduced, resulting in an increase in number of pores remaining in the sintered body. Also, when the particle size distribution is not so narrow one as described above, the arrangement of particles in the green body does not become uniform to cause the local growth of particles, resulting in an increase in number of residual pores. Further, when a purity of alumina is less than 99.99 wt %, this becomes one factor which can cause mixing of foreign substances into a semiconductor product, or allows anomalous growth of particles due to foreign substances to proceed, resulting in an increase in number of residual pores.

Also, in alumina powder with a primary particle size of 0.1 μm or less, the interaction between particles is strong to form aggregate particles, resulting in an increase in number of pores.

As the raw material of the present invention, an average particle size of alumina primary particles is preferably from 0.2 μm or more to 0.7 μm or less.

Examples of the alumina raw material of the present invention include AA02 (primary particle size of 0.2 μm), AA03 (primary particle size of 0.3 μm), AA04 (primary particle size of 0.4 μm), and AA07 (primary particle size of 0.7 μm), of SUMICORUNDUM manufactured by Sumitomo Chemical Co., Ltd. All of the purities thereof are 99.99 wt % or more.

Further, when the alumina powder used as a raw material has a purity of 99.99 wt % or more, said alumina powder may contain oxides or salts of elements other than aluminum in an amount of less than 0.01 wt %, or the substances such as water, organic substances and halogen elements in an amount of less than 1 parts by weight which are not spoiling the properties of the alumina sintered body of the present invention, and which can be removed from the raw material by heating at 1000° C. or less.

By using the above-described high purity alumina powder as a raw material, uniform arrangement of particles in the green body, high fired density, and uniform proceeding of growth of the particles in the whole sintered body can be achieved. This reduces pores to be left behind in the sintered body grains, or the grain boundaries. Further, local anomalous growth of particles due to impurities in the raw material will not proceed, and hence pores will not remain. Consequently, a high fired density of 3.970 g/cm$^2$ or more can be obtained. Further, a sintering agent is added if required for achieving still higher fired density. This inhibits the growth of grain boundary at the final stage of sintering to remove pores. As a result of such an effect and the like, a sintered body with a high fired density of 3.975 g/cm$^3$ or more can be obtained.

Examples of the sintering agent include one or more compounds selected from the group consisting of alkaline earth metal compounds and silicon compounds. Examples of the alkaline earth metal compound and silicon compound include oxides, nitrates, acetates, hydrides, chlorides, and alkoxides thereof. However, they are not limited thereto as long as they become oxides at a temperature of 1200° C. or less during sintering in an atmosphere. Concrete examples of the alkaline earth metal include Mg, Ca, Sr, and Ba. As the sintering agent, a magnesium compound is preferable, and magnesium nitrate is particularly preferable. The amount thereof to be added is generally from 10 ppm or more to 2000 ppm or less in terms of oxides, and preferably from 10 ppm or more to 700 ppm or less. Each of the above-described compounds becomes oxide during sintering in an atmosphere, and exerts its effect as sintering agent. When a sintered body with an alumina purity of 99.99 wt % or more is required depending upon its use, the sintering agent is added to the alumina powder in an amount of from 10 ppm or more to 150 ppm or less, more preferably of from 10 ppm or more to 70 ppm or less, in terms of oxide.

The process for producing a slurry will now be described below. First, the above-described alumina raw material powder, a solvent, and a dispersant are blended in appropriate amounts with mechanical stirring and mixing. In this step, there have been commonly and widely used the mixing methods using grinding media, i.e., the grinding methods using devices generally referred to as ball mill, vibration mill, pearl mill, attriter, and the like. However, the slurry production method of the present invention is characterized in that the alumina powder used as a raw material in the present invention undergoes less aggregates, and has uniform particle shape and particle size. Accordingly, the alumina powder can be dispersed to form a uniform slurry by irradiating with ultrasonic wave from the outside using a ultrasonic bath, or irradiating with ultrasonic wave by means of a ultrasonic homogenizer. The dispersion method not using medium such as ceramics ball is preferred in terms of avoiding mixing of oxides or salts other than aluminum. As for the ultrasonic wave, the irradiation ability is preferably 10 kHz or more, more preferably 25 kHz or more, in the case of a bath volume of 40 liters. The stirring and mixing time varies depending upon the volume of the slurry. For example, when the amount of slurry is 10 liters, stirring and mixing is preferably performed for 30 minutes or more. The raw material powder is sufficiently dispersed, and then organic binder is mixed therein. For example, when the amount of slurry is 10 liters, the mixing is preferably performed for one hour or more. It suffices only to perform mechanical stirring using an agitating blade even without ultrasonic irradiation.

The slurry prepared as described above can properly be deaerated under reduced pressure. Alternatively, various kinds of defoaming agents can also be used. Further, in accordance with the subsequent forming method, the viscosity may properly be set to be in the range of 50 to 10000 mPa/s by addition of various kinds of pH adjusters and flocculating agents. For example, in granulation by a spray dryer, the viscosity of the alumina slurry is preferably adjusted to be in the range of 300 to 400 mPa/s by pH adjustment with an aqueous solution of hydrochloric acid, aqueous ammonia, and the like for producing spherical granules. Further, the alumina concentration in the slurry can be increased by standing settling, centrifugal separation, and vacuum concentration by means of a rotary evaporator, and the like As a solvent, it varies depending upon the kind of binder to be used and the forming method. For polyvinyl alcohol and acrylic binder to be used when granules are produced by a spray dryer, water is most preferable. Various kinds of organic solvents can also be used according to the formulation. For example, a mixed solvent of toluene and butanol is preferable in doctor blade forming(also called tape casting).

As a dispersant, ammonium salt of polycarboxylic acid [ex., tradename; SN-D5468, manufactured by San Nopco Co., Ltd.] is mainly used when the solvent is water. For organic solvent, ethyl oleate, sorbitan monooleate, sorbitan trioleate, polycarboxylic acid series, and the like are used. For the alumina raw material powder to be used as raw material in the present invention, polyester series [tradename; TEXAPHOR 3012, manufactured by San Nopco Co., Ltd.] is preferable, but is not limited to these examples. The method not using a dispersant can provide a slurry with lower viscosity depending upon the organic binder to be used together.

Examples of the organic binder include polyvinyl alcohol, polyvinyl acetal, various kinds of acrylic polymers, methyl cellulose, polyvinyl acetate, polyvinyl butyral series, various kinds of waxes, and various kinds of polysaccharides, but is not limited to these examples.

The plasticizer varies depending upon the organic binder to be used. Examples thereof include ethylene glycol, diethylene glycol, polyethylene glycol, glycerin, polyglycerin, and various kinds of esters. Especially when an organic solvent is used, dibutyl phthalate, diethylhexyl phthalate and the like are used, but is not limited to these examples.

In the present invention, a mold-releasing agent, flocculating agent, pH adjuster can also be added as other additives. However, it is important that there are no inorganic impurities other than aluminium in solvents and additives. No addition of organic substances is most preferable as long as it presents no obstacles to shape retention of the green body, and handling on processing.

Examples of the forming means after drying the slurry include conventional methods such as slip casting pressurized slip casting, centrifugal casting, doctor blade forming, and extrusion forming. Alternatively, granules are produced by means of a spray dryer, or various kinds of pelletizing machines, after which dry forming methods such as pressing methods and cold isostatic press can be employed.

For the cold isostatic press, the above-described slurry is formed into granule by spray dry, or the like. The resulting granule is uniaxially pressed, preferably under a pressure in the range of 50 to 500 kg/cm², more preferably under a pressure in the range of 200 to 300 kg/cm². Thereafter, the resulting body is isotropically applied with a pressure preferably in the range of 0.5 to 3 t/cm², and more preferably in the range of 0.8 to 1.5 t/cm² by means of a cold isostatic press. Then, the resulting green body is processed into a prescribed form.

Alternatively, for example, for a small green body with a size of 20 mm or less, the raw material alumina powder can also be charged into a mold to carry out uniaxial press, or cold isostatic press under the above-described pressure.

The green bodies obtained by the above-described methods are subjected to the following process depending upon the size thereof. For example, for a green body 300 mmΦin diameter, and 30 mmt in thickness, it is calcinated at temperatures in the range of 500 to 1000° C. for 1 hour or more, and preferably in the range of 800 to 900° C. for 3 hours or more, to be removed organic materials. Thereafter, the resulting body is sintered in an air atmosphere at a temperature in the range of 1400 to 1800° C. for 1 hour or more, and preferably for 3 hours or more. Specifically, when the primary particle of the alumina raw material powder has a size of 0.7 $\mu$m, the sintering temperature is preferably 1650° C. or more. When the primary particle has a size of 0.2 $\mu$m, it is preferably 1450° C. or more.

The maximum pore diameter of pores in the sintered body obtained by the present invention is preferably 10 $\mu$m or less. The number of pores with a size of from 1 $\mu$m or more to 10 $\mu$m or less per one mm² is preferably 20 or less, more preferably 10 or less. Such high fired density of alumina sintered body can be obtained. In the alumina sintered body of the present invention, there less occur falling off of particles, and elution in the vicinity of pores during use as a component of a semiconductor manufacturing system on a thermal diffusion furnace, plasma etching process, or CVD system due to the low numbers of the pores. Further, the sintered body of the present invention has good corrosion resistance as a member to be in contact with a corrosive solution or gas. Further, there can be provided products with high reliability in terms of strength and wear resistance as bioceramic member of artificial tooth, artificial femoral head, and the like, mechanical components of bearing, thread guide, roller for rolling, pump component, and the like, and structural components of frame rod, core tube, shaft enclosing tube, and the like, owing to the low numbers of pores which are defects. Moreover, there can be provided decorative members such as plates and cups excellent in surface smoothness owing to no scattering of light due to pores.

Examples

Next, a description will now be given to the examples of the present invention, which is not construed as limiting the scope of the invention.

It is noted that various kinds of measurements in the present invention were carried out in the following manner.

(1) Measurement of number-average particle size of primary particles, and measurement of D/H of the primary particles The photographs of the powder particles were taken by means of a scanning electron microscope (SEM: manufactured by JEOL, Ltd. T-300 type). Fifty to hundred particles were selected from the photographs to conduct the image analysis thereof, thereby determining the values as the mean values.

(2) Measurement of D10 and D90 (measurement of weight cumulative particle size distribution; abbreviated as "particle size distribribution")

Measurement was carried out by means of a master sizer (manufactured by Malvern Co.,) by a laser diffraction scattering method. Alumina slurry for the measurement was prepared in the following manner. That is, 25 g of 0.5 wt % aqueous solution of sodium hexametaphosphate was added to 2.5 g of alumina powder. The resulting mixed solution was irradiated with ultrasonic wave by a homogenizer for 2 minutes to prepare the alumina slurry.

(3) Wet sieving

One kg of distilled water was added to one kg of alumina. Then, the resulting mixture was irradiated with ultrasonic wave with stirring for 30 minutes in a ultrasonic bath with a volume of 6 liters (frequency: 28 kHz, output: 200 W) to prepare a slurry. In a beaker filled with distilled water, 5 μm nylon mesh in bag form was immersed. The total amount of the alumina slurry previously prepared was flown into the nylon bag. Then, the whole beaker was irradiate with ultrasonic wave using a ultrasonic bath. This causes the alumina particles to pass through the nylon mesh and move into the beaker. Twenty minutes later, the nylon mesh bag was pulled up, and the outside of the bag was washed sufficiently, and dried to determine the amount of increase in weight. The amount of increase in weight was divided by the alumina charge of 1 kg, and the obtained value was taken as residue on the 5-μm sieve.

(4) Measurement of the number of pores and pore size on the polished surface of alumina sintered body The number of pores was determined as follows: that is, the photograph (magnification: 50 times) of the mirror-polished surface of a sintered body was taken using a light microscope (manufactured by Olympus Optical Co., Ltd.; BH-2). The number of pores occurring as black points in the photograph were counted visually to be converted into the number per $mm^2$. The alumina sintered body was first subjected to coarse grinding with a #800 diamond grinding wheel, resulting in a plane surface. Thereafter, the mirror polishing was carried out using 3-μm polycrystalline diamond slurry and a copper table polishing machine (high press lapping system manufactured by NIHON ENGIS Co.). Polishing was carried out for 60 minutes or more with the surface pressure during polishing being set at 300 $g/cm^2$ or more. For removing scratches on the surface, polishing was further conducted for 30 minutes or more with 1-μm polycrystalline diamond slurry. For a pore of not a circular shape, but of elliptical or indefinite shape, the measurement of the pore size was carried out taking the maximum diameter or the major axis of the diagonal line of the pore as pore size.

(6) Measurement of fired density of an alumina sintered body The fired density of a sintered body was measured according to the Archimedes method.

(7) Corrosion test

The corrosion test was carried out as follows: that is, the sintered body with its surface polished obtained by the above-described method was immersed in 80° C. nitric acid for 50 hours. Then, the pore on the surface was observed under light microscope to determine the amount of increase in area of the pore by means of an image analysis apparatus.

(8) Analysis of purity of alumina sintered body (ICP-AES quantitative determination method)

The alumina sintered body was ground in a boron nitride mortar, followed by alkali fusion. The fused material was subjected to ICP emission spectral analysis (ICP quantometer SPS1200VR type manufactured by Seiko Electronic Industry Co., Ltd.).

Example 1

The results are shown in Table 1.

In this example 1, α alumina powder (tradename SUMI-CORUNDUM AA04) manufactured by Sumitomo Chemical Co. Ltd., was used as raw material. The alumina powder is comprised of polyhedral particles each substantially not having a fractured surface and having 8 to 20 phases. The primary particle size thereof determined from the SEM photograph was found to be 0.4 μm. From the results of the particle size distribution measurement, D90 was found to be 1.48 μm, D10 was found to be 0.31 μm, and D90/D10 was found to be 4.8. The residue on the sieve of wet sieving was found to be in an amount of 5 ppm.

Five kg of the alumina powder AA04, 3 kg of water (solvent), and 62.5 g of a dispersant, ammonium polycarboxylate [manufactured by San Nopco Co, Ltd.; tradename SN-D5468] were mixed with stirring for 30 minutes while being irradiated with ultrasonic wave. Then, 750 g of 10 wt % solution of polyvinyl alcohol (manufactured by Kuraray Corp.; tradename PVA205c) as organic binder, 25 g of polyethylene glycol (reagent; degree of polymerization 400) as plasticizer, and 140 g of stearic acid emulsion [manufactured by CHUKYO YUSHI Co., Ltd; tradename CELOSOL 920] as lubricant were added in total amounts simultaneously, followed by 60-min of stirring and mixing, resulting in a slurry.

To the resulting slurry, was added 110 ml of 1N aqueous solution of hydrochloric acid to adjust the viscosity to 350 cP. The thus prepared slurry was subjected to spray drying by means of a spray dryer to produce granules. The resulting granule powder was charged into a mold, which was then formed under a load of 1500 $kg/cm^2$ by means of a uniaxial press machine. This resulted in a cylindrical green body with a diameter of 20 mm and a height of 10 mm. Then, the green body thus]produced was removed organic materials at900° C. for 3 hours, followed by sintering in an atmosphere at 1650° C. for 2 hours.

The density of the sintered body was found to be 3.974 $g/cm^3$. There was observed no pore with a size of more than 10 μm, and the number of pores each with a maximum diameter between 1 μm and 10 μm, both inclusive, was found to be 12 per $mm^2$, on the mirror-polished surface of the sintered body.

It was also found that, the amounts of the impurities of the sintered body were as follows: Fe: 5 ppm, Si: 5 ppm, Ca$\leq$1 ppm, Mg$\leq$1 ppm, Na$\leq$5 ppm, and other elements: less than the amount of detection limit (less than 1 ppm), and the total amount of elements other than Al: less than 50 ppm.

The pore occupied area after the corrosion test was found to be 0.02%.

Example 2

One hundred g of the alumina powder AA04 of example 1, 6.0 g of water, and 1.3 g of a dispersant SN-D5468 were mixed with stirring for 30 minutes while being irradiated with ultrasonic wave.

The resulting slurry was allowed to stand under reduced pressure for 30 minutes, to be deaerated. Further, a green body 30 mm wide, 50 mm long and 5 mm high was produced by slip casting utilizing a plaster mold. The resulting green body was sintered at 1650° C. for 2 hour.

The density of the sintered body was found to be 3.977 $g/cm^3$. There was observed no pore with a size of more than 10 μm, and the number of pores each with a maximum diameter between 1 μm and 10 μm, both inclusive, was found to be 18 per mm², on the mirror-polished surface of the sintered body.

It was also found that, the amounts of the impurities of the sintered body were as follows: Fe: 9 ppm, Si: 5 ppm, Ca≦1 ppm, Mg≦1 ppm, Na≦5 ppm, and other elements: less than the amount of detection limit (less than 1 ppm), and the total amount of elements other than Al: less than 50 ppm.

The pore occupied area after the corrosion test was found to be 0.02%.

Example 3

In this example 3, α alumina powder (tradename SUMICORUNDUM AA02) manufactured by Sumitomo Chemical Co., Ltd., was used as raw material. The alumina powder is comprised of polyhedral particles each substantially not having a fractured surface and having 8 to 20 phases. The primary particle size thereof determined from the SEM photograph was found to be 0.2 μm. From the results of the particle size distribution measurement, D90 was found to be 1.08 μm, D10 was found to be 0.18 μm, and D90/D10 was found to be 6.0. The residue on the sieve of wet sieving was found to be in an amount of 5 ppm.

Granules were produced under the same conditions as those in example 1, except that the alumina powder AA02 was used as raw material. A cylindrical green body was produced from the granules under the same conditions as those in example 1. Then, the green body thus produced was removed organic materials at 900° C. for 3 hours, followed by sintering in an atmosphere at 1550° C. for 2 hours.

The density of the sintered body was found to be 3.975 g/cm³. There was observed no pore with a size of more than 10 μm, and the number of pores each with a maximum diameter between 1 μm and 10 μm, both inclusive, was found to be 15 per mm², on the mirror-polished surface of the sintered body.

It was also found that, the amounts of the impurities of the sintered body were as follows: Fe: 6 ppm, Si: 9 ppm, Ca≦1 ppm, Mg≦1 ppm, Na≦5 ppm, and other elements: less than the amount of detection limit (less than 1 ppm), and the total amount of elements other than Al: less than 50 ppm.

The pore occupied area after the corrosion test was found to be 0.02%.

Example 4

In this example 4, α alumina powder (tradename SUMICORUNDUM AA03) manufactured by Sumitomo Chemical Co., Ltd., was used as raw material. The alumina powder is comprised of polyhedral particles each substantially not having a fractured surface and having 8 to 20 phases. The primary particle size thereof determined from the SEM photograph was found to be 0.33 μm. From the results of the particle size distribution measurement, D90 was found to be 1.38 μm, D10 was found to be 0.26 μm, and D90/D10 was found to be 5.0. The residue on the sieve of wet sieving was found to be in an amount of 10 ppm.

The alumina powder whose primary particle size was 0.33 μm was charged into a mold, which was then formed under a load of 200 kg/cm² by means of a uniaxial press machine. This resulted in a cylindrical green body with a diameter of 20 mm and a height of 10 mm. Then, the green body thus produced was subjected to cold isostatic press under a pressure of 1.0 t/cm². The green body was defatted at 900° C. for 3 hours, followed by sintering in an atmosphere at 1600° C. or 2 hours.

The density of the sintered body was found to be 3.980 g/cm³. There was observed no pore with a size of more than 10 μm, and the number of pores each with a maximum diameter between 1 μm and 10 μm, both inclusive, was found to be 5 per mm², on the mirror-polished surface of the sintered body.

It was also found that, the amounts of the impurities of the sintered body were as follows: Si: 8 ppm, Na≦5 ppm, and other elements: less than the amount of detection limit (less than 1 ppm), and the total amount of elements other than Al: less than 50 ppm.

The pore occupied area after the corrosion test was found to be 0.01%.

Example 5

In this example 5, α alumina powder (tradename SUMICORUNDUM AA07) manufactured by Sumitomo Chemical Co. Ltd., was used as raw material. The alumina powder is comprised of polyhedral particles each substantially not having a fractured surface and having 8 to 20 phases. The primary particle size thereof determined from the SEM photograph was found to be 0.7 μm. From the results of the particle size distribution measurement, D90 was found to be 2.08 μm, D10 was found to be 0.57 μm, and D90/D10 was found to be 3.6. The residue on the sieve of wet sieving was in an amount of 4 ppm.

Five kg of the alumina powder AA07, 3 kg of water, and 62.5 g of a dispersing agent, SN-D5468 were mixed with stirring for 30 minutes while being irradiated with ultrasonic wave. Then, 250 g of 40 wt % solution of acrylic emulsion [manufactured by Dainippon Ink & Chemicals Inc.; tradename BONCOAT3981] as organic binder, 140 g of CELOSOL 920 as lubricant were added in total amounts simultaneously, followed by 60-min of stirring and mixing, resulting in a slurry.

Granules and a molded body were produced under the same conditions as those in example 1, except that the resulting slurry was used. Then, the green body was removed organic materials at 900° C. for 3 hours, followed by sintering in an atmosphere at 1750° C. for 2 hours.

The density of the sintered body was found to be 3.971 g/cm³. There was observed no pore with a size of more than 10 μm, and the number of pores each with a maximum diameter between 1 μm and 10 μm, both inclusive, was found to be 15 per mm², on the mirror-polished surface of the sintered body.

It was also found that, the amounts of the impurities of the sintered body were as follows: Fe: 10 ppm, Na≦5 ppm, and other elements: less than the amount of detection limit (less than 1 ppm), and the total amount of elements other than Al: less than 50 ppm. The pore occupied area after the corrosion test was found to be 0.02%.

Example 6

In the process of producing the slurry of example 4, 6.4 g (200 ppm in terms of MgO) of magnesium nitrate hexahydrate (reagent grade) was added as sintering agent. Granules and a green body were produced under the same conditions as those in example 4. Then, the green body was removed organic materials at 900° C. for 3 hours, followed by sintering in an atmosphere at 1550° C. for 2 hours.

The density of the sintered body was found to be 3.984 g/cm³. There was observed no pore with a size of more than 10 μm, and the number of pores each with a maximum diameter between 1 μm and 10 μm, both inclusive, was found to be 7 per mm², on the mirror-polished surface of the sintered body.

The pore occupied area after the corrosion test was found to be 0.02%.

It was also found that, the amounts of the impurities of the sintered body were as follows: Fe: 5 ppm, Si: 5 ppm, Ca≦1 ppm, Mg: 125 ppm, Na≦5 ppm, and other elements: less than the amount of detection limit (less than 5 ppm), and the total amount of elements other than Al: less than 170 ppm.

Example 7

In the process of producing the slurry of example 1, 16.0 g (500 ppm in terms of MgO) of magnesium nitrate hexahydrate (reagent grade) was added as sintering agent. Granules and a green body were produced under the same conditions as those in example 1. Then, the green body was removed organic materials at 900° C. for 3 hours, followed by sintering in an atmosphere at 1600° C. for 2 hours.

The density of the sintered body was found to be 3.982 g/cm$^3$. There was observed no pore with a size of more than 10 μm, and the number of pores each with a maximum diameter between 1 μm and 10 μm, both inclusive, was found to be 4 per mm$^2$, on the mirror-polished surface of the sintered body.

The pore occupied area after the corrosion test was found to be 0.01%.

It was also found that, the amounts of the impurities of the sintered body were as follows: Fe: 9 ppm, Si: 8 ppm, Ca≦1 ppm, Mg: 305 ppm, Na≦5 ppm, and other elements: less than the amount of detection limit (less than 1 ppm), and the total amount of elements other than Al: less than 350 Ppm.

Example 8

In the process of producing the slurry of example 3, 1.6 g(50 ppm in terms of MgO) of magnesium nitrate hexahydrate (reagent grade) was added as sintering agent. Granules and a green body were produced under the same conditions as those in example 3. Then, the green body was removed organic materials at 900° C. for 3 hours, followed by sintering in an atmosphere at 1600° C. for 2 hours.

The density of the sintered body was found to be 3.982 g/cm$^3$. There was observed no pore with a size of more than 10 μm, and the number of pores each with a maximum diameter between 1 μm and 10 μm, both inclusive, was found to be 5 per mm$^2$, on the mirror-polished surface of the sintered body.

The pore occupied area after the corrosion test was found to be 0.01%.

It was also found that, the amounts of the impurities of the sintered body were as follows: Fe: 9 ppm, Si: 8 ppm, Ca≦1 ppm, Mg: 25 ppm, Na≦5 ppm, and other elements less than the amount of detection limit (less than 1 ppm), and the total amount of elements other than Al: less than 50 ppm.

Example 9 (Slip casting)

One hundred g of the a alumina powder AA04 of example 1, 60 g of water, 1.3 g of a dispersing agent SN-D5468, and 0.01 g of MgO (manufactured by Ube Material Co., Ltd; tradename 500A) were mixed with stirring for 30 minutes while being irradiated with ultrasonic wave. The MgO was to flow into a plaster mold in about half amount during slip casting, and hence MgO was added in an amount of 1000 ppm, corresponding to twice the amount thereof added.

The resulting slurry was allowed to stand under reduced pressure for 30 minutes, to be deaerated. Further, a green-body 30 mm wide, 50 mm long and 5 mm high was produced by slip casting utilizing a plaster mold. The resulting green body was sintered at 1600° C. for 2 hour.

The density of the sintered body was found to be 3.983 g/cm$^3$. There was observed no pore with a size of more than 10 μm, and the number of pores each with a maximum diameter between 1 μm and 10 μm, both inclusive, was found to be 4 per mm$^2$, on the mirror-polished surface of the sintered body.

The pore occupied area after corrosion test was found to be 0.02%.

It was also found that, the amounts of the impurities of the sintered body were as follows: Fe: 5 ppm, Si: 12 ppm, Ca: 5 ppm, Mg: 305 ppm, Na≦5 ppm, and other elements: less than the amount of detection limit (less than 5 ppm), and the total amount of elements other than Al: less than 350 ppm.

Example 10

In the process of producing the slurry of example 7, the amount of magnesium nitrate hexahydrate to be added as sintering agent was changed to 32.0 g (1000 ppm in terms of MgO) to produce granules. Then, a green body and further a sintered body were produced in the same manner as in example 7.

The density of the sintered body was found to be 3.980 g/cm$^3$. There was observed no pore with a size of more than 10 μm, and the number of pores each with a maximum diameter between 1 μm and 10 μm, both inclusive was found to be 5 per mm$^2$, on the mirror-polished surface of the sintered body.

The pore occupied area after the corrosion test was found to be 0.01%.

It was also found that, the amounts of the impurities of the sintered body were as follows: Fe: 5 ppm, Si: 8 ppm, Ca≦1 ppm, Mg: 600 ppm, Na≦5 ppm, and other elements: less than the amount of detection limit (less than 5 ppm), and the total amount of elements other than Al: less than 650 ppm.

Example 11

(Doctor blade forming also called tape casting)

In this example 11, a alumina powder (tradename SUMICORUNDUM AA05) manufactured by Sumitomo Chemical Co., Ltd., was used as raw material. The alumina powder is comprised of polyhedral particles each substantially not having a fractured surface and having 8 to 20 phases. The primary particle size thereof determined from the SEM photograph was found to be 0.5 μm. From the results of the particle size distribution measurement, D90/D10 was found to be 4.5. The residue on the sieve of wet sieving was in an amount of 3 ppm.

Five hundred g of AA05, 0.25 g of MgO, 308 g of toluene, 90 g of ethanol, 43 g of cyclohexanone, and 10 g of polyester dispersant (manufactured by San Nopco Co., Ltd.; tradename TEXAPHOR 3112) were mixed for 16 hours in a ball mill. Further, 36 g of polyvinyl butyral (manufactured by Sekisui Chemical Co., Ltd: tradename BL-S) and 18 g of dibutyl phthalate were added and mixed for 6 hours in a ball mill to obtain a homogeneous slurry. The viscosity of the slurry was adjusted by solvent removal, followed by film forming according to a doctor blade forming.

The resulting film was dried in air at room temperature for 96 hours, and then was cut into pieces each with a prescribed size. The resulting piece was calcined in an air atmosphere in an electric furnace. Then, the calcined body was defatted at 500° C. for 1 hour, followed by sintering at 1550° C. for 1 hour.

The density of the sintered body was found to be 3.982 g/cm³. There was observed no pore with a size of more than 10 μm, and the number of pores each with a maximum diameter between 1 μm and 10 μm, both inclusive was found to be 6 per mm², on the mirror-polished surface of the sintered body.

The pore occupied area after the corrosion test was found to be 0.02%.

It was also found that, the amounts of the impurities of the sintered body were as follows: Fe: 5 ppm, Si: 8 ppm, Ca≦1 ppm, Mg: 305 ppm, Na≦5 ppm, and other elements: less than the amount of detection limit (less than 1 ppm), and the total amount of elements other than Al: less than 350 ppm.

Example 12

In the process of producing the slurry of example 5, 3.6 g(100 ppm in terms of MgO) of magnesium nitrate hexahydrate was added as sintering agent to produce a slurry. Granules and a molded body were produced in the same manner as in example 5. Then, the green body was removed organic materials at 900° C. for 3 hours, followed by sintering in an atmosphere at 1700° C. for 2 hours.

The density of the sintered body was found to be 3.980 g/cm³. There was observed no pore with a size of more than 10 μm, and the number of pores each with a maximum diameter between 1 μm and 10 μm, both inclusive, was found to be 6 per mm², on the mirror-polished surface of the sintered body.

The pore occupied area after the corrosion test was found to be 0.01%.

It was also found that, the amounts of the impurities of the sintered body were as follows: Fe: 5 ppm, Na≦5 ppm, Mg: 60 ppm, and other elements: less than the amount of detection limit (less than 1 ppm), and the total amount of elements other than Al: less than 110 ppm.

Example 13

A green body and a sintered body were produced in the same manner as in example 7, except that the amount of magnesium nitrate hexahydrate added as sintering agent was changed to 3.6 g (50 ppm in terms of MgO) to produce granules in example 7.

The density of the sintered body was found to be 3.981 g/cm³. There was observed no pore with a size of more than 10 μm, and the number of pores each with a maximum diameter between 1 μm and 10 μm, both inclusive, was found to be 7 per mm², on the mirror-polished surface of the sintered body.

The pore occupied area after the corrosion test was found to be 0.01%.

It was also found that, the amounts of the impurities of the sintered body were as follows: Fe: 5 ppm, Si: 8 ppm, Ca≦1 ppm, Mg: 35 ppm, Na≦5 ppm, and other elements: less than the amount of detection limit (less than 1 ppm), and the total amount of elements other than Al: less than 80 ppm.

Example 14

A green body and a sintered body were produced in the same manner as in example 7, except that the amount of magnesium nitrate hexahydrate added as sintering agent was changed to 1.8 g (25 ppm in terms of MgO) to produce granules in example 7.

The density of the sintered body was found to be 3.982 g/cm³. There was observed no pore with a size of more than 10 μm, and the number of pores each with a maximum diameter between 1 μm and 10 μm, both inclusive, was found to be 4 per mm², on the mirror-polished surface of the sintered body.

The pore occupied area after the corrosion test was found to be 0.01%.

It was also found that, the amounts of the impurities of the sintered body were as follows: Fe: 5 ppm, Si: 8 ppm, Ca≦1 ppm, Mg: 20 ppm, Na≦5 ppm, and other elements: less than the amount of detection limit (less than 1 ppm), and the total amount of elements other than Al: less than 70 ppm.

Comparative Example 1

(Slip casting)

In this comparative example 1, alumina raw material powder [manufactured by Showa Denko K. K.; UA5055] of which the purity is 99.99 wt % and the primary particle size is 0.3 μm was used. The primary particle of the alumina powder is a particle not of polyhedral shape, but of indefinite shape. The D/H was found to be larger than 2. From the observation of the particle by a tunnel electron microscope, it was found that the particle had a large number of defects within the particle. From the results of the particle size distribution measurement, D90 was found to be 2.55 μm, D10 was found to be 0.44 μm, and D90/D10 was found to be 5.8. The residue on the sieve of wet sieving was found to be in an amount of 120 ppm.

One hundred g of the alumina powder, 60 g of water, and 1.3 g of a dispersant SN-D5468 were mixed with stirring for 30 minutes while being irradiated with ultrasonic wave. The resulting slurry was used to carry out forming and sintering under the same conditions as in example 2.

The density of the sintered body was found to be 3.935 g/cm³. There was observed 65 pores each with a size of more than 10 μm per mm², and an infinite number of pores each with a maximum size of 10 μm, or less, on the mirror-polished surface of the sintered body.

Comparative Example 2

Five kg of the alumina powder UA5055 of the comparative example 1, 3 kg of water, and 65 g of a dispersant SN-D5468 were mixed with stirring for 30 minutes while being irradiated with ultrasonic wave. The resulting slurry was subjected to a ball mill treatment by means of a 2 mmΦ alumina ball. The ball milling time was set at 2 hours. Further, 1000 g of 10 wt % solution of PVA205c as organic binder, and 140 g of lubricant Cellosol 920 were added in total amounts simultaneously, followed by 60-min of stirring and mixing. This resulted in a slurry.

The resulting slurry was used to produce granules and the green body under the same conditions as those in example 1. Then, the green body was sintered under the same conditions as in example 1.

The density of the sintered body was found to be 3.945 g/cm³. There was observed 50 pores each with a size of more than 10 μm per mm², and an infinite number of pores each with a maximum size of 10 μm, or less, on the mirror-polished surface of the sintered body.

Comparative Example 3

Five g of the alumina powder UA5055 of the comparative example 1 was charged into a mold, which was then formed under a load of 300 kg/cm² by means of a uniaxial press machine. This resulted in a cylindrical green body with a diameter of 20 mm and a height of 10 mm. Then, the green body thus produced was subjected to cold isostatic press under a pressure of 3.0 t/cm². The green body obtained was defatted at 900° C. for 3 hours, followed by sintering in an atmosphere at 1750° C. for 2 hours.

The density of the sintered body was found to be 3.950 g/cm³. There was observed 35 pores each with a size of more than 10 μm per mm², and an infinite number of pores each with a maximum size of 10 μm, or less, on the mirror-polished surface of the sintered body.

Comparative Example 4

Granules and the green body were produced in the same manner as in example 7, except that the alumina powder UA5055 of the comparative example 1 was used as raw material. Then, sintering was carried out at 1550° C. for 2 hours.

The density of the sintered body was found to be 3.972 g/cm³. There was observed 34 pores each with a size of more than 10 μm per mm², and an infinite number of pores each with a maximum size of 10 μm, or less, on the mirror-polished surface of the sintered body.

The pore occupied area after the corrosion test was found to be 0.5%.

Comparative Example 5

In this comparative example 5, α alumina powder (tradename; SUMICORUNDUM AA2) manufactured by Sumitomo Chemical Co. Ltd., was used as raw material. The alumina powder is comprised of polyhedral particles each substantially not having a fractured surface and having 8 to 20 phases. The primary particle size thereof determined from the SEM photograph was found to be 2 μm. From the results of the particle size distribution measurement, D90 was found to be 2.08 μm, D10 was found to be 0.57 μm, and D90/D10 was found to be 3.6. The residue on the sieve of wet sieving was in an amount of 50 ppm. Granules and the green body were produced in the same manner as in example 7 using the alumina powder of this comparative example, followed by sintering at 1700° C. for 2 hours.

The density of the sintered body was found to be 3.900 g/cm³. There was observed 46 pores each with a size of more than 10 μm per mm², and an infinite number of pores each with a maximum size of 10 μm, or less, on the mirror-polished surface of the sintered body.

The pore occupied area after the corrosion test was found to be 0.7%.

Comparative Example 6

The alumina powder AA04 of the example 1 was subjected to heat treatment at 1400° C. The primary particle of this alumina is a polyhedron, which aggregates on heat treatment. The D90/D10 of the particle size distribution was found to be 10.

The residue on the sieve of wet sieving was found to be in an amount of 209 ppm. Granules, the green body, and the sintering body were produced in the same manner as in example 7, except that the alumina powder of this comparative example was used as raw material.

The density of the sintered body was found to be 3.900 g/cm³. There was observed 69 pores each with a size of more than 10 μm per mm², and an infinite number of pores each with a maximum size of 10 μm, or less, on the mirror-polished surface of the sintered body.

The pore occupied area after the corrosion test was found to be 0.9%.

Comparative Example 7

In this comparative example 7, Bayer process alumina powder of which the purity is 99.99 wt % and the primary particle size is 0.6 μm was used as raw material. The primary particle of the alumina powder is a particle not of polyhedral shape, but of indefinite shape. The D/H was found to be larger than 3. For the particle size distribution, D90/D10 was found to be 6.6. The residue on the sieve of wet sieving was found to be in an amount of 790 ppm. Granules, the molded body, and the sintered body were produced in the same manner as in example 7, except that the alumina powder of this comparative example was used as raw material.

The density of the sintered body was found to be 3.870 g/cm³. There was observed a large number of pores each with a size of more than 10 μm on the mirror-polished surface.

The pore occupied area after the corrosion test was found to be 2.1%.

Comparative Example 8

In this comparative example 8, an organoaluminium compound was hydrolyzed to prepare aluminium hydride, followed by sintering at 1000° C. The resulting alumina powder of which the purity is 99.99 wt % and the primary particle size is 0.5 μm was used as raw material. The primary particle of the alumina powder is a particle not of polyhedral shape, but of indefinite shape. The D/H was found to be 5. For the cumulative particle size distribution of the alumina powder, D90/D10 was found to be 5.8. Wet sieving was impossible. Granules, and the green body were produced in the same manner as in example 7, except that the above-described alumina powder was used as raw material.

The density of the sintered body was found to be 3.800 g/cm³. There was observed an infinite number of pores each with a size of more than 10 μm on the mirror-polished surface.

The pore occupied area after the corrosion test was found to be 2.3%.

The above-described examples and comparative examples reveal as follows:

(1) When a prescribed alumina particle is used as raw material, a high density and high purity alumina sintered body with extremely less pores can be produced by a dispersion method without using a grinding medium.

(2) When alumina particles other than the ones prescribed in the present invention are used as raw material, a high density and high purity alumina sintered body with extremely less pores cannot be produced by a dispersion method without using a grinding medium. Even if the molding pressure and sintering temperature are increased, the desired alumina sintered body cannot be produced (Comparative Examples 1, 2, 4, 7, and 8).

(3) When alumina particles other than the ones prescribed in the present invention are used as raw material, a high density and high purity alumina sintered body with extremely less pores cannot be produced even by a dispersion method using a grinding medium. (Comparative Examples 3).

(4) Even with alumina particles of the shape prescribed in the present invention, a high density alumina sintered body with extremely less pores cannot be produced in the case (Comparative Example 5) where the particle size is large, and the case (Comparative Example 6) where the particle size distribution is wide, and a large number of coarse particles are contained.

The present invention can provide an alumina sintered body which contains an extremely low amount of impurities and pores, and hence is suitable for the following items: that is, members to be in contact with a corrosive solution, gas, or the like, requiring corrosion resistance, such as products required to avoid mixing of other metallic elements, and adhesion or adsorption of dust particles, or the like, in the semiconductor industry (ex., materials for the products such as vacuum chuck, vacuum pincette, and hands for use in operations including cleaning, transferring, and surface processing of a silicon wafer, and further a polishing instrument for magnetic materials); or materials for the products required to avoid the presence of pores itself, (ex., materials for a substrate for a hard disk, and a substrate for a magnetic head, materials for various kinds of industrial mirrors, and a dummy wafer). Further, there can be provided products with high reliability in strength and wear resistance as bioceramic members, and various kinds of structural components owing to the low amount of pores, i.e., defects. Still further, there can be provided decorative members such as plates and cups excellent in surface smoothness owing to no scattering of light due to pores.

|  | Holding method | Sintering temperature ° C. | Density of sintered body g/cm$^3$ | Purity of sintered body Alumina % | Number of pores ≤10 μm | Number of pores ≥10 μm | Corrosion test | Pore area prior to corrosion % | Pore area subsequent to corrosion % |
|---|---|---|---|---|---|---|---|---|---|
| Example 1 | Press molding | 1650 | 3.974 | 99.99 | 12 | 0 | ○ | ≤0.01 | 0.02 |
| Example 2 | Slip press molding | 1650 | 3.977 | 99.99 | 18 | 0 | ○ | ≤0.01 | 0.02 |
| Example 3 | Press molding | 1550 | 3.975 | 99.99 | 15 | 0 | ○ | ≤0.01 | 0.02 |
| Example 4 | Press molding | 1600 | 3.980 | 99.99 | 5 | 0 | ○ | ≤0.01 | 0.01 |
| Example 5 | Press molding | 1750 | 3.971 | 99.99 | 15 | 0 | ○ | ≤0.01 | 0.02 |
| Example 6 | Press molding | 1550 | 3.984 | 99.98 | 7 | 0 | ○ | ≤0.01 | 0.02 |
| Example 7 | Press molding | 1600 | 3.982 | 99.95 | 4 | 0 | ○ | ≤0.01 | 0.01 |
| Example 8 | Press molding | 1600 | 3.982 | 99.99 | 5 | 0 | ○ | ≤0.01 | 0.01 |
| Example 9 | Slip press molding | 1600 | 3.983 | 99.95 | 4 | 0 | ○ | ≤0.01 | 0.02 |
| Example 10 | Press molding | 1600 | 3.980 | 99.90 | 5 | 0 | ○ | ≤0.01 | 0.01 |
| Example 11 | Tape molding | 1550 | 3.982 | 99.95 | 6 | 0 | ○ | ≤0.01 | 0.02 |
| Example 12 | Press molding | 1700 | 3.980 | 99.99 | 6 | 0 | ○ | ≤0.01 | 0.01 |
| Example 13 | Press molding | 1600 | 3.981 | 99.99 | 7 | 0 | ○ | ≤0.01 | 0.01 |
| Example 14 | Press molding | 1600 | 3.982 | 99.99 | 4 | 0 | ○ | ≤0.01 | 0.01 |
| Comparative example 1 | Slip press molding | 1600 | 3.935 | 99.99 | Large number | 65 | X | 0.08 | 0.5 |
| Comparative example 2 | Press molding | 1650 | 3.945 | 99.99 | Large number | 50 | X | 0.11 | 0.7 |
| Comparative example 3 | Press molding | 1750 | 3.950 | 99.99 | Large number | 35 | X | 0.15 | 0.9 |
| Comparative example 4 | Press molding | 1550 | 3.972 | 99.95 | Large number | 34 | X | 0.08 | 0.5 |
| Comparative example 5 | Press molding | 1700 | 3.900 | 99.95 | Large number | 46 | X | 0.11 | 0.7 |
| Comparative example 6 | Press molding | 1600 | 3.900 | 99.95 | Large number | 69 | X | 0.15 | 0.9 |
| Comparative example 7 | Press molding | 1600 | 3.870 | 99.50 | Large number | Large number | X | 0.17 | 2.1 |
| Comparative example 8 | Press molding | 1500 | 3.800 | 99.95 | Large number | Large number | X | 0.2 | 2.3 |

What is claimed is:

1. A process for producing a polycrystalline alumina sintered body which comprises the steps of:
    preparing a slurry by subjecting alumina powder and a solvent to ultrasonic irradiation, mechanical stirring not using a grinding medium, or ultrasonic irradiation and mechanical stirring not using a grinding medium, to provide a slurry of alumina dispersed in a solvent;
    drying and forming said slurry to produce a green body; and then
    sintering said green body in an air atmosphere at a temperature in the range of 1400° C. to 1800° C.;
    wherein said alumina powder has:
    a purity of 99.99 wt % or more and comprises a alumina particles having a polyhedral shape, each having substantially no fractured surface, and having a D/H ratio of from 0.5 or more to 3.0 or less, wherein D represents a maximum particle diameter parallel to the hexagonal lattice plane of a hexagonal close packed lattice of α alumina, and H represents a maximum particle diameter perpendicular to the hexagonal lattice plane of a hexagonal close packed lattice of α alumina;
    a number-average particle size of from 0.1 μm or more to 1.0 μm or less; and
    a D90/D10 ratio of 7 or less, wherein D10 and D90 are the particle sizes at 10% cumulation diameter and 90% cumulation diameter, respectively, from the smallest particle side in a cumulative particle size distribution.

2. The process according to claim 1, wherein an alumina powder in mixture with a sintering agent is subjected to ultrasonic irradiation, mechanical stirring not using a grinding medium, or ultrasonic irradiation and mechanical stirring not using a grinding medium, to provide a slurry of alumina dispersed in a solvent.

3. The process according to claim 1, wherein the maximum diameter of pores in said polycrystalline alumina sintered body is 10 μm or less, the number of said pores of from 1 μm or more to 10 μm or less per one mm$^2$ is 20 or less, said alumina purity is 99.99% or more, and the density of said sintered body is 3.970 g/cm$^3$ or more.

4. The process according to claim 2, wherein the maximum diameter of pores in said polycrystalline alumina sintered body is 10 μm or less, the number of said pores of from 1 μm or more to 10 μm or less per one mm$^2$ is 10 or less, said alumina purity is 99.99% or more, and the density of said sintered body is 3.975 g/cm$^3$ or more.

5. The process according to claim 2, wherein said sintering agent is added to said alumina powder in an amount of from 10 ppm or more to 2000 ppm or less in terms of oxide.

6. The process according to claim 2, wherein said sintering agent is added to said alumina powder in an amount of from 10 ppm or more to 70 ppm or less in terms of oxide.

7. The process according to claim 2, wherein said sintering agent is at least one compound selected from the group consisting of alkaline earth metal compounds and silicon compounds.

8. The process according to claim 2, wherein said sintering agent is a magnesium compound.

* * * * *